(12) United States Patent
Wada et al.

(10) Patent No.: US 7,692,003 B2
(45) Date of Patent: Apr. 6, 2010

(54) PENICILLIN CRYSTALS AND PROCESS FOR PRODUCING THE SAME

(75) Inventors: Isao Wada, Tokushima (JP); Yutaka Kameyama, Tokushima (JP)

(73) Assignees: Otsuka Chemical Co., Ltd., Osaka-shi; Taiho Pharmaceutical Co., Ltd., Tokyo (JP)

( * ) Notice: Subject to any disclaimer, the term of this patent is extended or adjusted under 35 U.S.C. 154(b) by 585 days.

(21) Appl. No.: 10/574,278

(22) PCT Filed: Oct. 8, 2004

(86) PCT No.: PCT/JP2004/015305

§ 371 (c)(1),
(2), (4) Date: Mar. 31, 2006

(87) PCT Pub. No.: WO2005/035539

PCT Pub. Date: Apr. 21, 2005

(65) Prior Publication Data

US 2006/0293516 A1 Dec. 28, 2006

(30) Foreign Application Priority Data

Oct. 9, 2003 (JP) ............................ 2003-350406

(51) Int. Cl.
*C07D 477/14* (2006.01)
(52) U.S. Cl. .................................................. 540/310
(58) Field of Classification Search .................. 540/310
See application file for complete search history.

(56) References Cited

U.S. PATENT DOCUMENTS

| | | | | |
|---|---|---|---|---|
| 4,496,484 A * | 1/1985 | Micetich et al. | ............ | 540/310 |
| 4,507,239 A | 3/1985 | Micetich et al. | ............ | 260/245 |
| 4,562,073 A | 12/1985 | Micetich et al. | ............ | 424/114 |
| 4,861,768 A | 8/1989 | Torii et al. | ............ | 514/195 |
| 4,898,939 A | 2/1990 | Torii et al. | ............ | 540/310 |
| 2004/0162277 A1* | 8/2004 | Shimbayashi et al. | ....... | 514/192 |
| 2007/0060559 A1* | 3/2007 | Tokumaru et al. | ............ | 540/310 |

FOREIGN PATENT DOCUMENTS

| | | |
|---|---|---|
| CA | 1201433 | 3/1986 |
| EP | 0092948 | 2/1983 |
| JP | 01-110689 | 4/1984 |
| JP | 8-505645 | 6/1996 |
| JP | 2002-53581 | 2/2002 |
| JP | 2002-53582 | 2/2002 |
| WO | WO 02/092605 | 11/2002 |

OTHER PUBLICATIONS

Li et al, Transactions of Tianjin University (2002), 8(1), 33-36.*
Micetich, Ronald G. et al., Synthesis (1986), (4), 292-6.*
Maiti, European Journal of Medicinal Chemistry (1994), 29(10), 795-8.*
Lin et al., Huaxue Gongye Yu Gongcheng (Tianjin, China) (2002), 19(3), 219-224, 273.*
Partial translation of Lin et al., Huaxue Gongye Yu Gongcheng (Tianjin, China) (2002), 19(3), 219-224, 273.*
Chen et al., Shanxi Daxue Xuebao, Ziran Kexueban (2001), 24(4), 329-330.*
Partial translation of Chen et al., Shanxi Daxue Xuebao, Ziran Kexueban (2001), 24(4), 329-330.*
Bai et al., Jingxi Huagong (2001), 18(11), 634-637.*
Partial translation of Bai et al., Jingxi Huagong (2001), 18(11), 634-637.*
Deng et al., Zhongguo Yaowu Huaxue Zazhi (2001), 11(2), 93-95.*
Partial translation of Deng et al., Zhongguo Yaowu Huaxue Zazhi (2001), 11(2), 93-95.*
Liu et al., Taiyuan Ligong Daxue Xuebao (2002), 33(6), 663-665.*
Partial translation of Liu et al., Taiyuan Ligong Daxue Xuebao (2002), 33(6), 663-665.*
Maiti et al; "Synthesis of Benzhydryl 2α-(Chloromethyl)-2β-methyl-6,6-dihydropenam-3α-carboxylate 1,1-Dioxide: The 2α-Isomer of the Potent β-Lactamase Inhibitor BL-P2013;" J.Org. Chem. 53 (1988) pp. 3803-3807.
Tanaka et al; "A facile Reductive Removal of Bromine Atom(s) of 6,6-Dibromo- and 6-Bromopenicillanate Derivatives in a Pb/Al Bimetal System;" Bull. Chem. Soc. Jpn. 62 (1989) pp. 627-629.
European Office Action dated Sep. 22, 2008.
Tanaka, Hideo et al: "A Facile Halogenative Cyclization of 4-(2-Benzothiazolyldithio)azetidinones (Kamiya's Disulfide) into 2β-(Halomethyl)penams in a Two Layer System," Bull. Chem. Soc. Jpn. 1989, 62 (9), 3046-3048.
"Vogel's Textbook of Practical Organic Chemistry," A. I. Vogel, Longman Publishers, New York 1989.

* cited by examiner

*Primary Examiner*—Mark L Berch
(74) *Attorney, Agent, or Firm*—Kratz, Quintos & Hanson, LLP

(57) ABSTRACT

The present invention provides 2β-chloromethyl-2α-methyl-penam-3α-carboxylic acid benzhydryl ester (CMPB) crystals of excellent stability, and a process for producing the CMPB crystals comprising the steps of (A) concentrating a solution containing CMPB; (b) subjecting the thus-obtained concentrate to column chromatography; (C) concentrating a CMPB-containing fraction; and (D) dissolving the thus-obtained CMPB-containing concentrate in an ether solvent and adding a hydrocarbon solvent to the resulting solution to precipitate CMPB crystals.

2 Claims, 2 Drawing Sheets

PENICILLIN CRYSTALS AND PROCESS FOR PRODUCING THE SAME

TECHNICAL FIELD

The present invention relates to penicillin crystals and a process for producing the same.

BACKGROUND OF THE INVENTION

Formula (1)

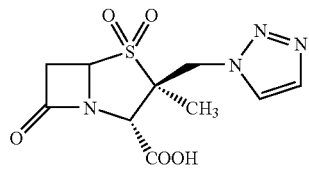

(1)

Tazobactam, which is represented by Formula (1) given above, exhibits very weak antibacterial activity, and it is therefore not used alone as an antibacterial agent. However, it irreversibly binds to various β-lactamases produced by microorganisms and exhibits an ability to inhibit β-lactamase activities. Hence, tazobactam is used in combination with various existing antibacterial agents that are inactivated by β-lactamases, allowing such antibacterial agents to exhibit their inherent antibacterial activity against β-lactamase-producing microorganisms (Katsuji SAKAI, *Recent Antibiotics Manual*, 10th ed., page 113).

2β-chloromethyl-2α-methylpenam-3α-carboxylic acid benzhydryl ester (hereinafter sometimes referred to as "CMPB") has a chemical structure represented by Formula (2):

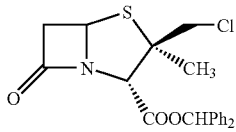

(2)

wherein Ph is phenyl.

As shown in the reaction scheme below, tazobactam is produced from CMPB via triazolylation at the 2'-position, oxidization at the 1-position and deesterification at the 3-position. Therefore, CMPB is of use as an intermediate for synthesizing tazobactam.

Reaction Scheme:

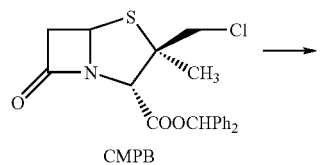

CMPB

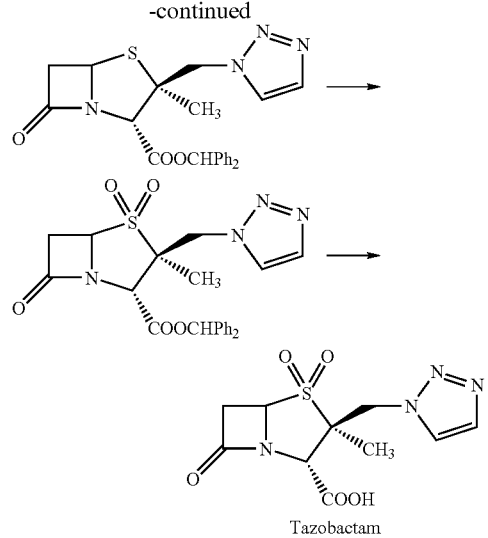

Tazobactam

CMPB is usually produced, for example, according to a process in which 2-oxo-4-(benzothiazol-2-yl)dithio-α-isopropenyl-1-azetidine acetic acid benzhydryl ester is reacted with a hydrohalogenic acid in a solvent in the presence of a nitrous acid salt and/or a nitrous acid ester (see Japanese Patent No. 2602669), or according to a process in which 2-oxo-4-(benzothiazol-2-yl)dithio-α-isopropenyl-1-azetidine acetic acid benzhydryl ester is reacted with a copper chloride in a solvent (see U.S. Pat. No. 4,496,484)

CMPB obtained according to the processes disclosed in Japanese Patent No. 2602669 and U.S. Pat. No. 4,496,484 is in the form of an oil (see Comparative Examples 1 and 2 below). Such CMPB is problematic in that it is unstable due to the presence of a halogen atom, which is easily eliminated, in the molecule. For example, once stored at ordinary temperatures (room temperature), CMPB as obtained according to the aforementioned processes undergoes degradation in a relatively short period of time so that the quality thereof is severely deteriorated.

A high degree of stability is desired in intermediates for synthesizing pharmaceuticals such that the intermediates do not undergo decomposition, deterioration, etc., under mild and economical conditions as in storage at ordinary temperatures, enabling their initial qualities to be maintained over a long period of time. Accordingly, a high degree of stability is desired in CMPB as well.

DISCLOSURE OF THE INVENTION

An object of the present invention is to provide CMPB crystals of excellent stability.

The inventors conducted extensive research to solve the problem described above and, as a result, succeeded in recovering CMPB crystals of excellent stability, by concentrating a CMPB-containing solution, subjecting the thus-obtained concentrate to column chromatography, concentrating the CMPB-containing fraction thus obtained, and treating the CMPB-containing concentrate with specific solvents. The present invention has been accomplished based on these findings.

The present invention provides the crystals and process as described in the following items 1 to 4:

1. Crystals of 2β-chloromethyl-2α-methylpenam-3α-carboxylic acid benzhydryl ester.

2. Crystals according to Item 1 that have peaks at the following interplanar spacings in the X-ray powder diffraction pattern obtained by a copper radiation of λ=1.5418 Å through a monochromator:

d (Interplanar spacings)
 7.27-8.16
 5.36-5.93
 4.44-4.92
 3.64-4.37

3. Crystals according to Item 1 that have peaks at the following interplanar spacings in the X-ray powder diffraction pattern obtained by a copper radiation of λ=1.5418 Å through a monochromator:

d (Interplanar spacings)
 7.2787-8.1577
 5.3646-5.9292
 4.4430-4.9106
 3.6423-4.3602

4. A process for producing crystals of 2β-chloromethyl-2α-methylpenam-3α-carboxylic acid benzhydryl ester comprising the steps of:

(A) concentrating a solution containing 2β-chloromethyl-2α-methylpenam-3α-carboxylic acid benzhydryl ester (CMPB);

(B) subjecting the thus-obtained concentrate to column chromatography;

(C) concentrating a CMPB-containing fraction; and (D) dissolving the thus-obtained CMPB-containing concentrate in an ether solvent and adding a hydrocarbon solvent to the resulting solution to precipitate CMPB crystals.

The CMPB crystals of the present invention can be produced by carrying out, for example, Steps (A) to (D) below:

Step A

CMPB-containing solutions usable in this step are known and include CMPB-containing reaction solutions obtained according to the processes disclosed in, for example, Japanese Patent No. 2602669 and U.S. Pat. No. 4,496,484.

CMPB-containing solutions can be concentrated according to known concentration techniques. An example of such a concentration technique is concentration under reduced pressure. The temperature during concentration should not exceed 50° C., and it is preferably from −10 to 30° C., and more preferably from 15 to 25° C.

The extent of concentrating CMPB-containing solutions is such that purification by column chromatography in Step B is not adversely affected.

Prior to Step A, it is preferable to remove insoluble materials from the CMPB-containing solution by filtration.

Step B

The concentrate obtained in Step A is purified by column chromatography.

Known column chromatography, e.g., silica gel column chromatography, can be used in this step.

Silica gel is not limited, and a variety of commercially available products such as Wakogel C-200 (manufactured by Wako Pure Chemical Industries, Ltd.), Silicagel 60 (manufactured by Merck, Ltd.) are usable.

Although the amount of silica gel varies depending on the diameter of the column to be used and other such factors, it is usually from about 2 to about 200 parts by weight and preferably from about 10 to about 100 parts by weight per part by weight of CMPB to be treated.

Developing solvents are those that are usually used in column chromatography, and include, benzene, toluene, and like aromatic hydrocarbons; methyl acetate, ethyl acetate, and like esters; acetone, methyl ethyl ketone, di-n-butyl ketone, and like ketones; acetonitrile; dichloromethane, dichloroethane, chloroform, carbon tetrachloride, and like halogenated hydrocarbons; diethyl ether, dioxane, tetrahydrofuran, and like ethers; n-hexane, and like aliphatic hydrocarbons, cyclohexane, and like alicyclic hydrocarbons, etc. Such solvents can be used singly, or two or more of such solvents may be combined in a suitable proportion for use.

A preferable example of developing solvents is a mixture of ethyl acetate and benzene. The volume ratio of ethyl acetate/benzene in the mixture is usually from about 1/10 to about 1/30 and preferably from about 1/15 to about 1/25.

The amount of developing solvent can be suitably selected according to the amount of CMPB to be treated, the amount of silica gel to be used, the type of developing solvent to be used, etc.

CMPB-containing fractions obtained in this step are collected and used in the following Step C.

Step C

The CMPB-containing fraction obtained in Step B can be concentrated according to known concentration techniques. An example of such a concentration technique is concentration under reduced pressure. The temperature during concentration should not exceed 50° C., and it is preferably from −10 to 30° C., and more preferably from 15 to 25° C.

Although it is desirable to remove as much of solvents contained in the CMPB-containing fraction as possible, it is sufficient that the CMPB-containing fraction is concentrated to have a solvent content of no more than 80 vol. %, preferably no more than 60 vol. %, and more preferably no more than 50 vol. %.

Step D

CMPB crystals are precipitated by dissolving the CMPB-containing concentrate obtained in Step C in an ether solvent and then adding a hydrocarbon solvent thereto.

Known ether solvents that can dissolve CMPB can be used in this step. Examples of preferable ether solvents are diethyl ether, diisopropyl ether, etc. Such ether solvents can be used singly or in combination.

The amount of ether solvent is such that the CMPB-containing concentrate is fully dissolved in the ether solvent. It is usually from about 0.5 to about 5 liters and preferably from about 0.80 to about 3 liters per kg of CMPB contained in the CMPB-containing concentrate. It is preferable to use the ether solvent in a volume equal to or greater than the volume of the solvent contained in the CMPB-containing concentrate.

The temperature during dissolution of the CMPB-containing concentrate in the ether solvent is usually from about −30 to about 50° C. and preferably from about −10 to about 30° C.

Known hydrocarbon solvents that do not readily dissolve CMPB can be used in this step. Examples of such hydrocarbon solvents are n-pentane, n-hexane, n-heptane, n-octane and like aliphatic hydrocarbons, cyclohexane and like alicyclic hydrocarbons, etc. Among such hydrocarbon solvents, aliphatic hydrocarbons are preferable, with n-hexane being particularly preferable.

The amount of hydrocarbon solvent is such that CMPB is precipitated. It is usually sufficient that the hydrocarbon solvent is gradually added in a total weight from about 0.1 to about 20 times and preferably about 0.5 to about 10 times the weight of the ether solvent used.

The temperature at which the hydrocarbon solvent is added is, in view of precipitation efficiency, usually from about −30 to about 50° C. and preferably from about −10 to about 30° C.

CMPB crystals generated by precipitation can be separated from the ether solvent and the hydrocarbon solvent according to conventional separation techniques. Examples of such separation techniques are filtration, centrifugation, etc. Filtration can be carried out under atmospheric pressure, increased pressure, or reduced pressure.

In the process of the invention, it is preferable to perform Steps A to D successively as promptly as possible.

EFFECTS OF THE INVENTION

The CMPB crystals of the present invention are stable despite the presence of a halogen atom, which is easily eliminated, in the molecule and do not undergo decomposition, deterioration, etc., after room temperature storage longer than one month, enabling the initial quality to be maintained.

Moreover, even when the CMPB crystals of the invention are dissolved in an organic solvent, e.g., dichloromethane, CMPB is extremely stable over a long period of time, not substantially undergoing decomposition. Hence, the triazolylation at the 2'-position, as shown in the reaction scheme above, of the crystalline CMPB of the invention can give the desired triazolylated compound in an enhanced yield.

Therefore, the crystalline CMPB of the invention can be suitably used as an intermediate for synthesizing pharmaceuticals such as tazobactam.

BEST MODE FOR CARRYING OUT THE INVENTION

An example, a reference example, comparative examples and test examples are given below to describe the invention in more detail.

Reference Example 1

To a dichloromethane solution of 45.8 g of 2-oxo-4-(benzothiazol-2-yl)dithio-α-isopropenyl-1-azetidine acetic acid benzhydryl ester (240 ml) were added 48.6 ml of a 35% hydrochloric acid and 48.5 ml of 5° C. water while ice cooling. An 36% aqueous sodium nitrite solution (18 ml) was then added dropwise over 30 minutes. The mixture was then stirred for 1 hour while ice cooling, the precipitate was filtered off, and the organic layer of the filtrate was separated. The organic layer was washed twice with cold water, dried over magnesium sulfate, and concentrated under reduced pressure, thereby giving 40 g of a foamy material.

A $^1$H-NMR spectral analysis revealed that the foamy material was of CMPB. A clear X-ray powder diffraction pattern was not obtained by copper radiation of λ=1.5418 Å through a monochromator, thereby revealing that the foamy material was amorphous CMPB.

Figure 1:
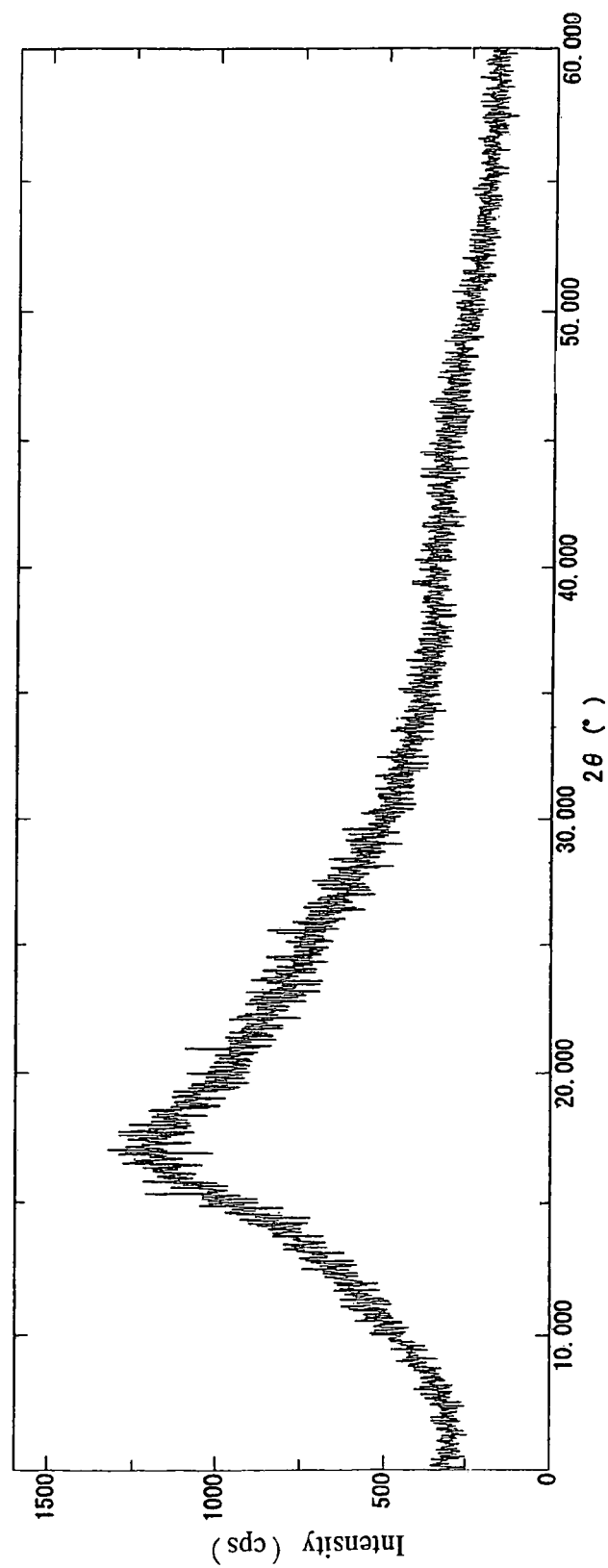
FIG. 1 is the x-ray powder diffraction pattern of the foamy material obtained in Reference Example 1.

FIG. 1 shows the x-ray powdery diffraction pattern of the foamy material obtained above.

Example 1

Step A

To a dichloromethane solution of 45.8 g of 2-oxo-4-(benzothiazol-2-yl)dithio-α-isopropenyl-1-azetidine acetic acid benzhydryl ester (240 ml) were added 48.6 ml of a 35% hydrochloric acid and 48.5 ml of 5° C. water while ice cooling. A 36% aqueous sodium nitrite solution (18 ml) was then added dropwise over 30 minutes. The mixture was then stirred for 1 hour while ice cooling, the precipitate was filtered off, and the organic layer of the filtrate was separated. The organic layer was washed twice with cold water, dried over magnesium sulfate, and concentrated under reduced pressure until the amount of dichloromethane in the organic layer was 40 ml.

Step B

The concentrate thus obtained was subjected to silica gel chromatography (filler: Wakogel C-200, 1 kg, developing solvent: benzene/ethyl acetate=20/1 by volume) to obtain CMPB-containing fractions. CMPB-containing fractions obtained were collected.

Step C

The collected CMPB-containing fraction was promptly concentrated at 20° C. under reduced pressure until the amount of solvent contained in the concentrate decreased to about 10 vol. %.

Step D

To the CMPB-containing concentrate thus obtained was added 50 ml of diethyl ether at 20° C. to give a solution. To this solution was gradually added 100 ml of n-hexane, thereby precipitating crystals.

The precipitated crystals were recovered by reduced-pressure filtration, washed with n-hexane and dried under reduced pressure at room temperature. The yield was 16.4 g.

A $^1$H-NMR spectral analysis verified that the crystals were of CMPB.

$^1$H-NMR (300 MHz, CDCl$_3$, δ ppm): 1.33 (s, 3H), 3.12 (dd, J=2 Hz, 16 Hz, 1H), 3.60 (s, 1H), 3.61 (dd, J=4 Hz, 16 Hz, 1H), 5.13 (s, 1H), 5.26, 5.34 (ABq, J=13 Hz, 2H), 5.41 (dd, J=2 Hz, 4 Hz, 1H), 7.25-7.40 (m, 10H)

A clear X-ray powder diffraction pattern of the crystals was obtained by copper radiation of λ=1.5418 Å through a monochromator as shown below:

| d (Interplanar spacings) | Relative intensities (I/I$_0$) |
|---|---|
| 9.461 | 0.21 |
| 7.769 | 0.50 |
| 7.662 | 0.51 |
| 6.506 | 0.35 |
| 5.647 | 1.00 |
| 5.248 | 0.29 |
| 4.761 | 0.30 |
| 4.677 | 0.40 |
| 4.358 | 0.25 |
| 4.275 | 0.28 |
| 4.153 | 0.51 |
| 3.907 | 0.19 |
| 3.834 | 0.36 |
| 3.448 | 0.26 |
| 3.200 | 0.19 |

Figure 2:
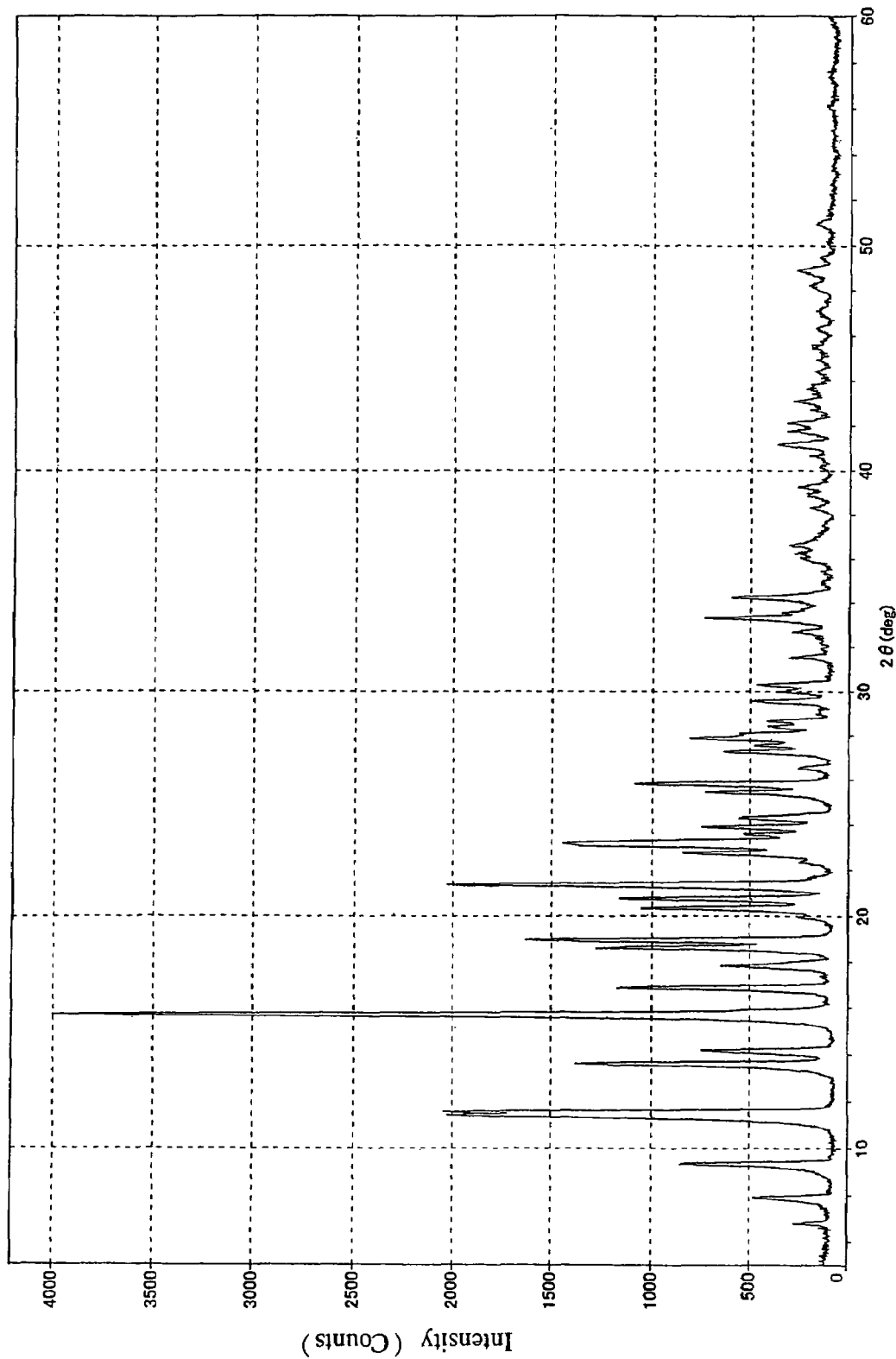
FIG. 2 is the x-ray powder diffraction pattern of the CMPB crystals obtained in Example 1.

FIG. 2 shows the X-ray powder diffraction pattern of the crystals.

Comparative Example 1

To a foamy material as obtained in Reference Example 1 (20 g) was added acetone to dissolve it in the acetone.

Insoluble materials were removed by filtration. The filtrate was concentrated, and 25 ml diethyl ether was added to the concentrate to attempt precipitation.

However, precipitation of solids was not observed and the solution stayed homogenous. To the solution was further gradually added n-hexane, but precipitation of solids was not observed and an oily material eventually appeared.

Comparative Example 2

A foamy material as obtained in Reference Example 1 (40 g) was dissolved in 40 ml dichloromethane and subjected to silica gel chromatography (filler: Wakogel C-200, 1 kg, developing solvent: benzene/ethyl acetate=20/1 by volume). The CMPB-containing fraction was promptly concentrated at 20° C. under reduced pressure, thereby giving an oily material.

A $^1$H-NMR spectral analysis revealed that the oily material was of CMPB.

Test Example 1

Five grams of the crystalline CMPB obtained in Example 1 (purity: 100%) and 5 g of the amorphous CMPB obtained in Reference Example 1 (purity: 99.2%) were placed in respective test tubes. These test tubes were sealed and stored at room temperature (20 to 30° C.) for 1 month. The respective purities of the CMPB samples were then determined using liquid chromatography.

The results revealed that the purity of the crystalline CMPB of Example 1 was 95%. The crystalline CMPB of Example 1 did not undergo significant decomposition, deterioration, etc., maintaining its initial quality. On the other hand, the purity of the amorphous CMPB of Reference Example 1 was 67%. The amorphous CMPB of Reference Example 1 lacked stability.

Test Example 2

One gram of crystalline CMPB (purity: 97%) prepared by storing the crystalline CMPB of Example 1 for 20 days at room temperature (about 25° C.) and 1.244 g of amorphous CMPB (purity: 78%) prepared by storing the amorphous CMPB of Reference Example 1 for 20 days at room temperature (about 25° C.) were used as test samples. Each sample was placed in flasks and 10 ml dichloromethane was added to dissolve the sample. These flasks were sealed. The dichloromethane solutions of CMPB samples were stirred at room temperature (about 25° C.) and, after 3.5 hours and after 5 hours, subjected to liquid chromatography to measure the amounts of CMPB remaining in the solutions. The amounts of the remaining CMPB were compared with the amount of CMPB in the crystalline CMPB sample or the amount of CMPB in the amorphous CMPB sample, which were measured prior to the test.

The results revealed that the amounts of the CMPB in the dichloromethane solution of crystalline CMPB sample after 3.5 hours and after 5 hours were exactly the same as the initial amount of CMPB in the crystalline CMPB, showing that the CMPB did not decompose in dichloromethane. On the other hand, the amounts of the CMPB in the dichloromethane solution of amorphous CMPB sample after 3.5 and 6 hours were 86.8% and 63.4%, respectively, of the initial amount of CMPB in the amorphous CMPB, showing that the CMPB in dichloromethane gradually decomposed.

The invention claimed is:
1. Crystals of 2β-chloromethyl-2α-methylpenam-3α-carboxylic acid benzhydryl ester.
2. A process for producing crystals of 2β-chloromethyl-2α-methylpenam-3α-carboxylic acid benzhydryl ester comprising the steps of:
   (A) concentrating a solution containing 2β-chloromethyl-2α-methylpenam-3α-carboxylic acid benzhydryl ester (CMPB);
   (B) subjecting the thus-obtained concentrate to column chromatography;
   (C) concentrating a CMPB-containing fraction; and
   (D) adding the thus-obtained CMPB-containing concentrate to an ether solvent and then adding the resultant solution to a hydrocarbon solvent to precipitate CMPB crystals.

* * * * *